US009789134B2

(12) United States Patent
Akhmedov et al.

(10) Patent No.: US 9,789,134 B2
(45) Date of Patent: Oct. 17, 2017

(54) AGENT FOR THE SELECTIVE ADJUSTMENT OF BLOOD LIPIDS

(71) Applicants: Federal State Budgetary Scientific Institution "Research Institute for Cardiology", Tomsk (RU); National Research Tomsk Polytechnic University, Tomsk (RU); Limited Liability Company "Nanocor", Tomsk (RU)

(72) Inventors: Shamil' D. Akhmedov, Tomsk (RU); Sergej A. Afanasiev, Tomsk (RU); Victor D. Filimonov, Tomsk (RU); Pavel S. Postnikov, Tomsk (RU); Marina E. Trusova, Tomsk (RU); Rostislav S. Karpov, Tomsk (RU)

(73) Assignees: FEDERAL STATE BUDGETARY SCIENTIFIC INSTITUTION "RESEARCH INSTITUTE FOR CARDIOLOGY", Tomsk (RU); NATIONAL RESEARCH TOMSK POLYTECHNIC UNIVERSITY, Tomsk (RU); LIMITED LIABILITY COMPANY "NANOCOR", Tomsk (RU)

( * ) Notice: Subject to any disclaimer, the term of this patent is extended or adjusted under 35 U.S.C. 154(b) by 0 days.

(21) Appl. No.: 15/094,646

(22) Filed: Apr. 8, 2016

(65) Prior Publication Data

US 2016/0220608 A1 Aug. 4, 2016

Related U.S. Application Data

(63) Continuation of application No. PCT/RU2013/001128, filed on Dec. 16, 2013.

(30) Foreign Application Priority Data

Oct. 8, 2013 (RU) .................................. 2013145065

(51) Int. Cl.
| | |
|---|---|
| *A61K 33/44* | (2006.01) |
| *A61K 9/14* | (2006.01) |
| *C07C 15/00* | (2006.01) |
| *B82Y 5/00* | (2011.01) |
| *A61K 9/51* | (2006.01) |
| *C01B 31/02* | (2006.01) |

(52) U.S. Cl.
CPC .............. *A61K 33/44* (2013.01); *A61K 9/145* (2013.01); *A61K 9/51* (2013.01); *B82Y 5/00* (2013.01); *C01B 31/0206* (2013.01); *C01B 31/0273* (2013.01); *C07C 15/00* (2013.01)

(58) Field of Classification Search
None
See application file for complete search history.

(56) References Cited

U.S. PATENT DOCUMENTS

| 7,033,975 B2 * | 4/2006 | Baran, Jr. .............. B82Y 30/00 166/268 |
| 7,871,533 B1 * | 1/2011 | Haiping ................. B82Y 30/00 252/402 |

FOREIGN PATENT DOCUMENTS

| RU | 2405655 C2 | 12/2010 |
| WO | 96/18688 | 6/1996 |

OTHER PUBLICATIONS

International Search Report from PCT/RU2013/001128, filed Dec. 16, 2013, dated Jun. 10, 2014.
Grundy, S.M. et al, Implications of Recent Clinical Trials for the National Cholesterol Education program Adult Treatment Panel III Guidelines, Circulation, 2004, pp. 227-239, No. 110.
Bosch, Thomas et al, Direct Adsorption of Low-Density Lipoprotein by DALI-LDL-Apheresis: Results of a Prospective Long-term Multicenter Follow-up Covering 12 291 Sessions, Therapeutic Apheresis and Dialysis, 2006, pp. 210-218, vol. 10, No. 3.
Yeh, Jiann-Horng et al, Plasmapheresis for Severe Lipemia: Comparison of Serum-Lipid Clearance Rates for the Plasma-Exchange and Double-Filtration Variants, Journal of Clinical Apheresis, 2003, pp. 32-36, v. 18.
Voinov, V.A., Efferent Therapy. Therapeutic plasmapheresis, Membrane plasmapheresis. Ecology and homeostasis. Infectious diseases. Chronic Diseases. Allergies, 1997, pp. 9-12, 75-80, 84-95.

* cited by examiner

*Primary Examiner* — Robert M Kelly
(74) *Attorney, Agent, or Firm* — Patentbar International, P.C.

(57) ABSTRACT

The invention relates to the medicine, namely to an agent for reducing the cholesterol and triglycerides in the blood plasma. The agent claimed comprises a nanocomposite that is a carbon-containing nanoparticles coated with the organic alkyl functional groups representing the residuals —$C_4H_9$, —$C_6H_{11}$, —$C_8H_{15}$, —$C_{10}H_{21}$, —$C_{16}H_{33}$, —$C_{18}H_{35}$. These groups are deposited by the covalent modification using diazonium salts of the general formula $XC_6H_4N_2^+Y^-$, where X is the alkyl residual —$C_4H_9$, —$C_6H_{11}$, —$C_8H_{15}$, —$C_{10}H_{21}$, —$C_{16}H_{33}$, or $C_{18}H_{35}$, Y is the anion $HSO_4^-$, $Cl^-$, $BF_4^-$ or $TsO^-$. The invention provides an effective reduction of cholesterol and triglyceride presented in the blood plasma.

1 Claim, No Drawings

AGENT FOR THE SELECTIVE ADJUSTMENT OF BLOOD LIPIDS

RELATED APPLICATIONS

This application is a Continuation of International Application No. PCT/RU2013/001128, filed on Dec. 16, 2013, which claims priority to Russian Patent Application No. RU 2013145065, filed on Oct. 8, 2013, both of which are incorporated herein by reference in their entirety.

FIELD OF THE INVENTION

The invention relates to the medicine and can be used to prepare new medical agents allowing the effective selective adjustment of cholesterol and triglycerides in the blood serum.

BACKGROUND OF THE INVENTION

At present it is proved that the disruption of the blood lipids, such as high level of cholesterol and triglycerides, is an unfavorable factor that increases the risk of cardiovascular diseases [1]. Thus, a high content of cholesterol and triglycerides in the blood adversely affects the outcome of surgical interventions aimed at the heart muscle vascularization.

In the practical medicine the patients with impaired blood lipid profile are recommended to observe the special diets and prescribed to use the appropriate medical therapy [2]. In far-advanced states it is necessary to perform the procedure for "forced" blood purification of excess cholesterol and triglycerides [2, 3]. For this purpose the patient's blood plasma shall be passed through the special filters in which there is the binding of the substances dissolved in the blood plasma, including cholesterol and triglycerides. The basis of such filters is composed of the sorbents capable of binding the substances dissolved in the plasma. The activated carbon and/or synthetic ion exchange resins are used as the sorbents. However, the presently used adsorbents do not have sufficient selectivity, and while contacting with them, the plasma not only loses excess cholesterol and triglycerides, but also ions and other substances contained in the plasma that degrades the chemical composition of the blood of the patients. This circumstance significantly reduces the effectiveness of the treatment and its possible application for a number of patients.

The prototype of this invention can be the sorbent obtained on the basis of activated carbon [4].

The disadvantage of this sorbent consists in the following:
1. This sorbent reacts with both the lipid profile and protein fractions of the blood plasma.
2. Do not have selectivity.

SUMMARY OF THE INVENTION

The object of the invention is to produce the agent allowing to selectively reduce the cholesterol and triglycerides in the blood liquid fraction.

The problem set shall be solved using a nanocomposite that is the carbon-containing nanoparticles with the organic functional groups of a lipophilic nature deposited on them representing the residues covalently bonded to the surface with the general formula $C_6H_4X$, where X is an alkyl residue having a carbon number value of 4 or more deposited by reaction of the carbon-containing nanoparticles with diazonium salts of the general formula $XC_6H_4N_2^+Y^-$, where Y is an anion ($HSO_4^-$, $Cl^-$, $BF_4^-$, $TsO^-$, etc.).

The technical result of the invention is production of the agent allowing to selectively reduce the cholesterol and triglyceride presented in the blood serum.

DETAILED DESCRIPTION OF THE PREFERRED EMBODIMENTS

The present invention has experimentally shown that a nanocomposite that is the carbon-containing nanoparticles with the organic functional groups of a lipophilic nature deposited on them representing the residuals covalently bonded to the surface with the general formula $C_6H_4X$, where X is an alkyl residue having a carbon number value of 4 or more, deposited by reaction of the carbon-containing nanoparticles with diazonium salts of the general formula $XC_6H_4N_2^+Y^-$, where Y is an anion ($HSO_4^-$, $Cl^-$, $BF_4^-$, $TsO^-$, etc.), may selectively reduce the levels of cholesterol and triglycerides in the blood serum.

Any information relating to the fact that the carbon-containing nanoparticles can affect the cholesterol and triglyceride in the liquid fraction of human blood have not been found in the patent, scientific and medical literature.

This property of the carbon-containing nanoparticles does not follow from the prior technical level in this field and is not obvious for a specialist.

The invention can be used to produce new and effective agent allowing the selective reduction of cholesterol and triglycerides in the blood in order to correct its lipid profile and possibly to prevent the progression of atherosclerosis in human body.

Based on the foregoing, it shall be assumed that the present invention complies with the following conditions of patentability: "Novelty", "Inventive level", "Industrial applicability".

The invention shall be understood on the basis of the following description.

The blood serum samples with the known content of cholesterol and triglycerides were combined with the nanocomposites representing the carbon-containing nanoparticles with the organic functional groups of a lipophilic nature deposited on them, containing the alkyl substituents —$C_4H_9$, —$C_6H_{11}$, —$C_8H_{15}$, —$C_{10}H_{21}$, —$C_{16}H_{33}$, —$C_{18}H_{35}$ with the concentration of 20 mg/ml and 80 mg/ml, then the samples were incubated for 30 minutes in a thermostatic shaker incubator and centrifuged at 4000 rev/min for 15 minutes at indoor temperature. The level of cholesterol and triglycerides was determined in the supernatant volume with the fermentation and colorimetric method.

Example

For production of nanocomposite it is necessary to use the aromatic diazonium salts, developed by one of the three following methods:

1. 0.684 g (3.6 mmol) of p-toluenesulfonic acid has been dissolved in 8 ml of glacial acetic acid, after complete dissolving it is necessary to add under vigorous stirring 0.371 ml (3.6 mmol) of tert-butyl nitrite. This solution shall be slowly combined with 3 mmol of an aromatic amine (4-butylaniline, 4-hexylanilint, 4-decylanilin, 4-dodecylaniline, 4-hexadecylanilin, 4-octadecylanilin, respectively). The control over reactions have been carried out by the TLC method (the eluent is benzene:ethanol 9:1) until dissolution of the initial aniline. After the reaction, the reaction mixture shall be combined with 100 ml of diethyl ether in order to have precipitation of the corresponding tosylate arenediazonium. The precipitate shall be dried in air at indoor temperature. The yield shall be 94-98%.

2. 3 mmol (4-butylaniline, 4-hexylanilint, 4-decylanilin, 4-dodecylaniline, 4-hexadecylanilin, 4-octadecylanilin, respectively) have been suspended in 15 ml of distilled water, followed by addition of 1.5 ml of 50% $HBF_4$. The stirring has been carried out at 12° C. The prepared aqueous solution $NaNO_2$ (3.3 mmol in 10 ml of distilled water) has been slowly added with vigorous stirring to the resulting reaction mixture. The resulting beige precipitate of the corresponding tetrafluoroborate arenediazonium shall be filtered and air dried. The yield shall be 94-96%.

3. 3 mmol (4-butylaniline, 4-hexylanilint, 4-decylanilin, 4-dodecylaniline, 4-hexadecylanilin, 4-octadecylanilin, respectively) and 1.5 ml of concentrated HCl have been suspended in 15 ml of distilled water, after formation of a white precipitate 6 mmol (0.414 g) of $NaNO_2$ have been added. While adding NaNCh the white precipitate has dissolved, resulting in a clear solution of the corresponding chloride arenediazonium. The control over reactions have been carried out by the TLC test (the eluent is benzene:ethanol 9:1) until dissolution of the initial aniline. In this case, the aqueous solution is used on the modification stage. The aromatic diazonium salt (0.02 g) has been dissolved in 15 ml of distilled water (acetonitrile), 0.03 g of the carbon-containing nanoparticles has been added. The resulting reaction mixture has been stirred vigorously and left at indoor temperature for 30 minutes. The product has been extracted from the reaction mixture using a magnet, an excess of the diazonium salt has been first washed with distilled water (acetonitrile) and then with methyl alcohol, acetone, and air dried. The obtained modified nanoparticles have the corresponding residue on the surface (4-butylbenzene, 4-hexylbenzene, 4-decylbenzene, 4-dodecylbenzene, 4-hexadecylbenzene, 4-octadodecylbenzene, respectively).

The ability of the modified nanocomposites to reduce cholesterol and triglycerides in the blood plasma of the patients of a cardia surgery nature has been evaluated in vitro as follows.

The blood sampling from the patients has been carried out in the fasted state from the ulnar vein by venipuncture into the special sterile vacuum systems <<BD Vacutainer®>> filled with $K_3$ EDTA in order to obtain blood plasma. Immediately after the receipt the plasma samples have been added to the microtubes with a pre-prepared weighted portions of the nanocomposites used.

We have performed three series of studies: using the unmodified carbon-containing nanoparticles (the 1st series); and using the nanocomposites representing the carbon-containing nanoparticles with the organic functional radicals of a lipophilic nature deposited on them: 4-butylbenzene (the 2nd series) and 4-octadodecylbenzol (the 3rd series). In all cases, the nanomaterial has been used in a concentration of 20 and 80 mg/ml.

The microtubes with samples have been incubated for 30 minutes in a thermostatic shaker incubator "Stat-fax 2200" at a temperature of +36.5° C. Then, they have been centrifuged for 15 minutes at 4000 rev/min and at indoor temperature in the centrifuge <<FP-510 Centrifuge>> (Labsystems, Finland). Investigation of the level of cholesterol and triglycerides have been carried out in the supernatant with the fermentative colorimetric method using the sets of the reactive chemicals made by Diacon-DS CJSC (Russia). The assessment and registration of the results have been carried out on a semi-automatic biochemical analyzer Clima MC-15 (Spain) at a wavelength of 500 nm. For each patient we have performed the preliminary control determination of cholesterol and triglycerides in the blood plasma. In order to assess the statistical significance of the differences detected we have used the Wilcoxon test.

According to data presented in the table, the addition of the unmodified carbon-containing nanoparticles to the samples have not lead to a reduction in cholesterol and triglycerides.

While using a nanocomposite that is the carbon-containing nanoparticles with the organic functional groups of a lipophilic nature deposited on them, a statistically significant reduction of cholesterol has been obtained already at a minimum concentration of nanocomposites (20 mg/ml). While using a higher concentration of nanocomposites (80 mg/ml), further enhancement of the effect has been noted.

While determining the content of triglycerides, we have not get their significant reduction at the nanocomposite concentration of 20 mg/ml. However, at the concentration of nanocomposites of 80 mg/ml we have obtained the reduction in the blood plasma triglycerides expressed up to 88%.

The results obtained indicate that after chemical modification the carbon-containing nanoparticles acquire the ability to reduce the levels of cholesterol and triglyceride in the blood plasma that is strengthening with increasing length of the alkyl residue. Thus, the blood protein fractions have remained unchanged.

Effect of nanoparticles on the level of total cholesterol and triglycerides in the EDTA blood plasma of patients with the lipid disorders

| Series of research and concentration of nanoparticles | | Parameters | |
|---|---|---|---|
| | | Cholesterol (mmol/l) | Triglycerides (mmol/l) |
| Control (without nanoparticles) | | 6.36 ± 0.38 | 2.90 ± 0.24 |
| 1st series | 20.0 mg/ml | 6.31 ± 0.25 | 2.90 ± 0.20 |
| | 80.0 mg/ml | 6.15 ± 0.26 | 2.87 ± 0.21 |
| 2nd series | 20.0 mg/ml | 5.95 ± 0.44 | 2.88 ± 0.21 |
| | 80.0 mg/ml | 5.34 ± 0.64* | 2.64 ± 0.22 |
| 3rd series | 20.0 mg/ml | 5.47 ± 0.36* | 2.88 ± 0.25 |
| | 80.0 mg/ml | 5.21 ± 0.38* | 2.58 ± 0.26* |

Note:
*statistically important value ($p < 0.05$) in comparison with the indicator without nanoparticles.

The invention can be used to produce new medical agents allowing the effective selective reduction in the cholesterol and triglycerides in blood.

REFERENCES

1. Thomas Bosch, Simon Gahr, Ulrike Belschner et al./Direct Adsorption of Low-Density Lipoprotein by DALI-LDL-Apheresis: Results of a Prospective Long-term Multicenter Follow-up Covering 12 291 Sessions/Therapeutic Apheresis and Dialysis. 2006, No. 10 (3), P. 210-218.

2. Jiann-Horng Yeh, May-Fen Lee, Hou-Chang Chiu./Plasmapheresis for Severe Lipemia: Comparison of Serum-Lipid Clearance Rates for the Plasma-Exchange and Double-Filtration Variants/Journal of Clinical Apheresis. 2003, No. 18, P. 32-36.

3. Grundy S. M., Cleeman J. L., Merz C. N. The coordinating committee of the national cholesterol education program/Circulation. 2004, No. 110, P. 227-239.

4. Voinov V. A. Effective therapy. Membrane plasmapheresis.—Saint-Petersburg: Esculap, 1997.—P. 9-12, 75-80, 84-95.

What is claimed is:

1. An agent for reducing cholesterol and triglycerides in blood plasma, the agent comprising a nanocomposite of carbon containing nanoparticles and organic residues deposited on the nanoparticles, the organic residues comprising an alkyl group selected from the group consisting of $-C_4H_9$, $-C_6H_{11}$, $-C_8H_{15}$, $-C_{10}H_{21}$, $-C_{16}H_{33}$, and $-C_{18}H_{35}$ deposited by covalent modification of the nanoparticles by diazonium salts with a general formula $XC_6H_4N_2^+Y^-$, wherein X is the alkyl group selected from the group consisting of $-C_4H_9$, $-C_6H_{11}$, $-C_8H_{15}$, $-C_{10}H_{21}$, $-C_{16}H_{33}$, and $-C_{18}H_{35}$, and wherein Y is an anion $HSO_4^-$, $Cl^-$, $BF_4^-$ or $TsO^-$.

* * * * *